US011974929B1

(12) United States Patent
Arabi et al.

(10) Patent No.: US 11,974,929 B1
(45) Date of Patent: May 7, 2024

(54) ELECTROMAGNETIZED EXTERNAL DEVICE FOR DYNAMIC REVERSIBLE FUSION OF THE SHOULDER

(71) Applicant: UNITED ARAB EMIRATES UNIVERSITY, Al Ain (AE)

(72) Inventors: Alya A. Arabi, Al Ain (AE); Bassem T. Elhassan, Boston, MA (US)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 18/200,172

(22) Filed: May 22, 2023

(51) Int. Cl.
*A61F 2/40* (2006.01)
*A61F 2/58* (2006.01)
*A61F 2/70* (2006.01)
*A61F 2/30* (2006.01)
*A61F 2/68* (2006.01)

(52) U.S. Cl.
CPC .............. *A61F 2/581* (2013.01); *A61F 2/40* (2013.01); *A61F 2/70* (2013.01); *A61F 2002/30052* (2013.01); *A61F 2002/30079* (2013.01); *A61F 2002/30538* (2013.01); *A61F 2002/30662* (2013.01); *A61F 2002/30668* (2013.01); *A61F 2002/4022* (2013.01); *A61F 2002/4085* (2013.01); *A61F 2002/6854* (2013.01); *A61F 2002/6863* (2013.01); *A61F 2002/701* (2013.01)

(58) Field of Classification Search
USPC ...................................................... 623/18.12
See application file for complete search history.

(56) References Cited

U.S. PATENT DOCUMENTS

| 7,101,374 | B2 | 9/2006 | Hyde, Jr. |
| 8,273,130 | B2 | 9/2012 | Gradl |
| 10,675,152 | B2 | 6/2020 | Cook et al. |
| 11,304,829 | B2 | 4/2022 | Mecklenburg et al. |
| 2020/0253737 | A1 | 8/2020 | Bonutti et al. |

FOREIGN PATENT DOCUMENTS

| DE | 102017201049 A1 | 7/2018 | |
| EP | 2813716 A1 | 12/2014 | |
| JP | 2006-026197 A * | 2/2006 | ............... A61F 2/38 |
| KR | 10-2021-0012976 A * | 2/2021 | ......... A61F 2/30749 |

OTHER PUBLICATIONS

Doursounian, Levon, et al. "Total shoulder replacement by magnetic arthroplasty." Journal of Shoulder and Elbow Surgery 7.1 (1998): 13-18.

* cited by examiner

*Primary Examiner* — David H Willse
(74) *Attorney, Agent, or Firm* — Nath, Goldberg & Meyer; Richard C. Litman

(57) ABSTRACT

A dynamic reversible electromagnetic locking element for locking the shoulder joint of a patient, in particular, in the form of a shoulder orthosis or a shoulder prosthesis, and methods for implementing the same. The dynamic reversible electromagnetic locking element has a ball and socket configuration to assist in operation of a glenohumeral joint (GHJ) in the patient.

19 Claims, 5 Drawing Sheets

ELECTROMAGNETIZED EXTERNAL DEVICE FOR DYNAMIC REVERSIBLE FUSION OF THE SHOULDER

BACKGROUND OF THE INVENTION

Field of the Invention

The disclosure of the present patent application relates to a dynamic reversible electromagnetic locking element for locking the shoulder joint. In particular, the present patent application relates to a shoulder orthosis or a shoulder prosthesis.

Description of Related Art

Management of shoulder pain and dysfunction secondary to nerve injuries around the shoulder can be very challenging. The motion of the arm is the result of the motion of the glenohumeral joint and the scapulothoracic articulation. The motion of these parts can be severely impaired in a patient suffering from nerve injuries around the shoulder.

Shoulder replacement evolved as the state of art treatment for shoulder pain secondary to arthritis with excellent outcomes. However, the current techniques for shoulder replacement require normal muscle functions around the shoulder girdle to achieve such a desirable outcome. When the muscles around the glenohumeral joint are dysfunctional or paralyzed, the outcome of shoulder replacement has been reported to be very poor.

There are fourteen muscles that work together to allow the arm to move fully. Six of these muscles work mostly on the glenohumeral shoulder joint and eight muscles work on the scapulo-thoracic articulation. The full motion of the shoulder is achieved by the combined motions of the glenohumeral joint (GHJ) and Scapulo-Thoracic Articulation (STA). In a simplified description, the distribution of motion is: ⅔ for the GHJ and ⅓ for the STA. In other words, if a patient can move their shoulder fully to 180° of flexion, 60° of this motion is contributed by the STA.

Before reverse shoulder arthroplasty was available, the management and outcome of patients with advanced shoulder arthritis, especially those with associated rotator cuff tear, were poor. With the introduction of reverse shoulder arthroplasty (RSA), good to excellent outcomes have been obtained that have been extensively reported in the literature. Based on most studies, close to 90% of patients receiving reverse shoulder arthroplasty report significant improvement of function and reduction of pain.

The reverse shoulder arthroplasty, in concept, reverses the normal glenohumeral joint articulation (the humerus has the sphere-like portion and the glenoid is the socket) to a design where the sphere is placed on the surface of the socket (glenoid) and the socket-like part of the articulation is placed through the humerus. This leads to a constrained joint instead of a loose unstable joint. For this reverse design to function well, a good functional deltoid is required to move the joint. If there is any rotator cuff remaining, it can help in shoulder rotation, but it is not necessary to achieve adequate shoulder function.

In patients who are candidates for reverse shoulder arthroplasty, but have a paralyzed or damaged deltoid, restoration of function remains extremely challenging. To obtain the desired shoulder function, these patients may require a major muscle transfer surgery to improve their shoulder elevation to 60-90°. Another way to achieve improved shoulder function is to fuse (glue) the GHJ at a certain elevated angle that will allow the STA to perform the motion.

Shoulder fusion can result in satisfactory outcomes in patients with nerve injuries around the shoulder, or in those patients who are candidates to receive reverse shoulder arthroplasty but cannot because of their lack of the deltoid muscle.

Another main disadvantage of shoulder fusion is that it is irreversible, and that it creates a fixed angle at which the shoulder is fused, which can improve certain aspects of the shoulder function while decreasing or eliminating other shoulder functions. For example, if the shoulder fusion is positioned at a higher elevation and external rotation, then the patient may be able to wash their hair and perform other activities of daily living that require the use of their hand in front of their body. However, it would be almost impossible for such patients to place their hand on their abdomen and impossible for them to reach behind their body.

In addition, most patients do not know what to expect from shoulder fusion surgery because there is no simple way to explain it to them. Further, if the shoulder fusion surgery is performed and the patient is unhappy with the results, there is nothing else that can be done, and the patient will remain that way for the rest of their lives. For this reason, an alternative simple surgical procedure was proposed that mimics shoulder fusion without doing the actual fusion surgery, to temporarily demonstrate to the patient the likely outcome of shoulder fusion. In this case, under general anesthesia, the shoulder is positioned in the proposed fusion position and pins are placed percutaneously across the joint to temporarily fix the joint. Following the surgery, the patients are awakened and encouraged to try to use their arm for few days to experience what it will feel like to have shoulder fusion surgery.

Surprisingly, 40% of patients did not like this alternative surgical procedure, the pins had to be removed, and other options had to be discussed. The remaining 60% of patients thought the alternative surgical procedure was good for them, though they reported that the fusion had many passive/active motion restrictions.

In order to maximize the potential range of motion that patients may have after fusion, while keeping it reversible, our idea aims to perform a dynamic fusion of the shoulder.

Accordingly, there is a need for new shoulder replacement procedures, devices, and systems allowing the patients to position their shoulder in any position they wish to have better performance. The present subject matter addresses these needs.

SUMMARY OF THE INVENTION

The present subject matter relates to a device, system, and method for performing dynamic, reversible shoulder fusion to maximize the potential range of motion that patients may have in their shoulder, post-fusion, while keeping the fusion reversible. Using the present device, system, and method, the patients can position their shoulder in any position they wish to achieve a better function, and then they can temporarily lock that shoulder position. Accordingly, the present subject matter relates to dynamic reversible fusion of the shoulder.

In this regard, the present shoulder replacement design is similar to the design of currently known shoulder replacements, specifically the reverse shoulder arthroplasty, only magnetized using an external device. This allows fixing of the shoulder at specific angles that can be controlled by the patient using the device, which potentially can allow significant improvement of shoulder motion, without restricting the passive motion of the shoulder and the ability to place the hand on the abdomen when the implant is unlocked. The ability of locking and unlocking the implant can decrease the risk of implant wear, pain around the scapulothoracic area, and allow for full passive motion of the shoulder totally under the control of the patient.

In an embodiment, the present subject matter relates to a reversible electromagnetic locking element having a ball and socket configuration assisting operation of a glenohumeral joint (GHJ) in a patient, comprising: a ball; an electromagnet; a microswitch; an energy source comprising a battery to power the electromagnet; and a socket with which the ball connects, wherein one of the ball and the socket is made of a magnetic metal or has the magnetic metal affixed thereto and the electromagnet is located with the other of the ball and the socket; wherein the microswitch can be used to selectively activate the electromagnet to exert an electromagnetic force between the ball and the socket such that the ball and the socket, once implanted in the patient to assist the glenohumeral joint of the patient, are locked via magnetism at a desired angular position about which an arm of the patient can freely move when in an on position and, when the microswitch is in an off position, deactivate the electromagnet to release the electromagnetic force between the ball and the socket, thereby unlocking the ball from the socket at the desired angular position about which the arm of the patient can freely move when the microswitch is in the on position. In certain embodiments, either one of the ball and socket can be made of metal and the other one can be made of a non-metal, or both of the ball and socket can be made of metal, i.e., a metal ball and/or a metal socket.

In another embodiment, the present subject matter relates to a method for improving range of motion of a damaged shoulder joint in a patient, the method comprising: replacing a shoulder of the patient with a reversible electromagnetic locking element having a ball and socket configuration to assist operation of a glenohumeral joint (GHJ) in the patient, the reversible electromagnetic locking element comprising a ball, an electromagnet, a microswitch, and a socket with which the ball connects, wherein one of the ball and the socket is configured to be attached to a shoulder blade of the patient and the other of the ball and the socket is configured to be attached to a head of a humerus of the patient, wherein one of the ball and the socket is made of a magnetic metal or has the magnetic metal affixed thereto and the electromagnetic field is generated with the other of the ball and the socket; providing an energy source comprising a battery to power the electromagnet; placing the glenohumeral joint at a desired angular position; selectively activating the electromagnet to exert an electromagnetic force between the ball and the socket such that the ball and the socket are locked via electromagnetism at a desired angular position about which an arm of the patient can freely move by switching the microswitch to an on position; and selectively deactivating the electromagnet to release the electromagnetic force between the ball and the socket, thereby unlocking the ball from the socket by switching the microswitch to an off position. Again, in certain embodiments, either one of the ball and socket can be made of metal and the other one can be made of a non-metal, or both of the ball and socket can be made of metal, i.e., a metal ball and/or a metal socket.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1A:
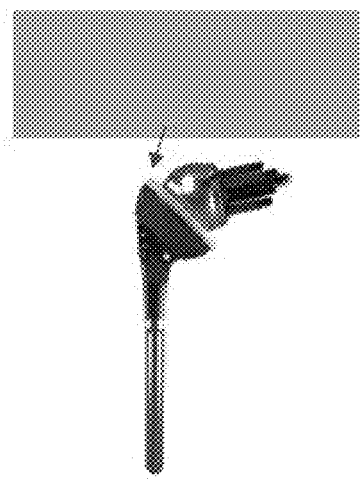
FIG. 1A shows a drawing of a prior art reverse shoulder arthroplasty (RSA) implant using polyethylene.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a device, system, and method for performing dynamic, reversible shoulder fusion to maximize the potential range of motion that patients may have in their shoulder, post-fusion, while keeping the fusion reversible. Using the present device, system, and method, the patients can position their shoulder in any position they wish to achieve a better function, and then they can temporarily lock that shoulder position. Accordingly, the present subject matter relates to dynamic reversible fusion of the shoulder.

In this regard, the present shoulder replacement design is similar to the design of currently known shoulder replacements, specifically the reverse shoulder arthroplasty, only magnetized using an external device. This allows fixing of the shoulder at specific angles that can be controlled by the patient using the device, which potentially can allow significant improvement of shoulder motion, without restricting the passive motion of the shoulder and the ability to place the hand on the abdomen when the implant is unlocked. The ability of locking and unlocking the implant can decrease the risk of implant wear, pain around the scapulothoracic area, and allow for full passive motion of the shoulder totally under the control of the patient.

Figure 1B:
FIG. 1B shows X-ray images of this RSA implant, in use.

In comparison to the prior art shoulder replacement of FIG. 1, the polyethylene portion, or any other suitable similar material, indicated by the arrow can instead be placed on a metallic portion of the ball or the conductive metal to act as an insulating thin layer, thereby avoiding any potential short circuit at the joint.

In an embodiment, one of the ball and the socket is made of, has affixed thereto, or comprises a magnetic metal. The other of the ball and the socket is made of, has affixed thereto, or comprises a conductive metal connected to a battery to generate an electromagnetic field. This conductive metal can either be embedded inside the ball or the socket (if the ball or the socket is made of a non-metal) or can be the ball or the socket itself in embodiments where the ball or the socket is made of a conductive metal. Accordingly, the magnetic metal of the ball or the socket is locked to the electromagnetic field generated by the other of the ball or the socket. These electromagnetic fields can be controlled by an external control device that could be an arm band, Bluetooth, or a remote sensor. In an embodiment, the external control device can switch the electromagnetic field on and off. If the external control device is in an "on" position, the battery is connected to the conductive metal and the electromagnetic field is generated. If the external control device is in an "off" position, the battery is not connected to the conductive metal and there is no electromagnetic field generated.

At rest, the electromagnetic field is switched off. When the patient wishes to use their shoulder actively, locking of the shoulder will depend on the type of activity. For instance, if patients wish to do overhead activities, their shoulder is positioned in flexion/external rotation and then the magnet is activated to lock the GHJ in that position. The patient might be able to reach flexion above 100 degrees and use this position throughout the day before unlocking the GHJ.

Accordingly, in an embodiment, the present subject matter relates to a reversible electromagnetic locking element having a ball and socket configuration assisting operation of a glenohumeral joint (GHJ) in a patient, comprising: a ball; an electromagnet; a microswitch; an energy source comprising a battery to power the electromagnet; and a socket with which the ball connects, wherein one of the ball and the socket is made of a magnetic metal or has the magnetic metal affixed thereto and the electromagnet is located with the other of the ball and the socket; wherein the microswitch can be used to selectively activate the electromagnet to exert an electromagnetic force between the ball and the socket such that the ball and the socket, once implanted in the patient to assist the glenohumeral joint of the patient, are locked via magnetism at a desired angular position about which an arm of the patient can freely move when in an on position and, when the microswitch is in an off position, deactivate the electromagnet to release the electromagnetic force between the ball and the socket, thereby unlocking the ball from the socket. When unlocked, the ball and the socket are disconnected from one another, and the motion control is lost. In certain embodiments, either one or both of the ball and socket can be made of metal, i.e., a metal ball and/or a metal socket.

In an embodiment of the present subject matter, the electromagnet can comprise a magnet and a conductive metal that can generate an electromagnetic field when connected to a battery.

In certain embodiments, the present reversible electromagnetic locking element can have one or more of the following configurations:
- the socket is a magnetic metal, and the conductive metal and the microswitch are located with the non-metal ball;
- the ball is a magnetic metal, and the conductive metal and the microswitch are located with the non-metal socket;
- the socket is a magnetic metal, and the ball is a conductive metal with one wire connecting the conductive metal to the microswitch and a second wire connecting the conductive metal to the energy source, wherein the energy source is connected to the microswitch, with both the energy source and the microswitch being located separately from the metal ball; and the ball is a magnetic metal, and the socket is a conductive metal with one wire connecting the conductive metal to the microswitch and a second wire connecting the conductive metal to the energy source, wherein the energy source is connected to the microswitch, with both the energy source and the microswitch being located separately from the metal socket.

According to these embodiments, metal of the metal ball or the metal socket can be used as the electromagnet to generate an electromagnetic field.

In any of the above embodiments, the switch can be but is not necessarily located inside the ball or metal; it can also be elsewhere, e.g., outside next to the battery, or even with the battery. Further, the battery can typically be located separately from the ball and the socket, just under the skin of the patient.

Figure 2:
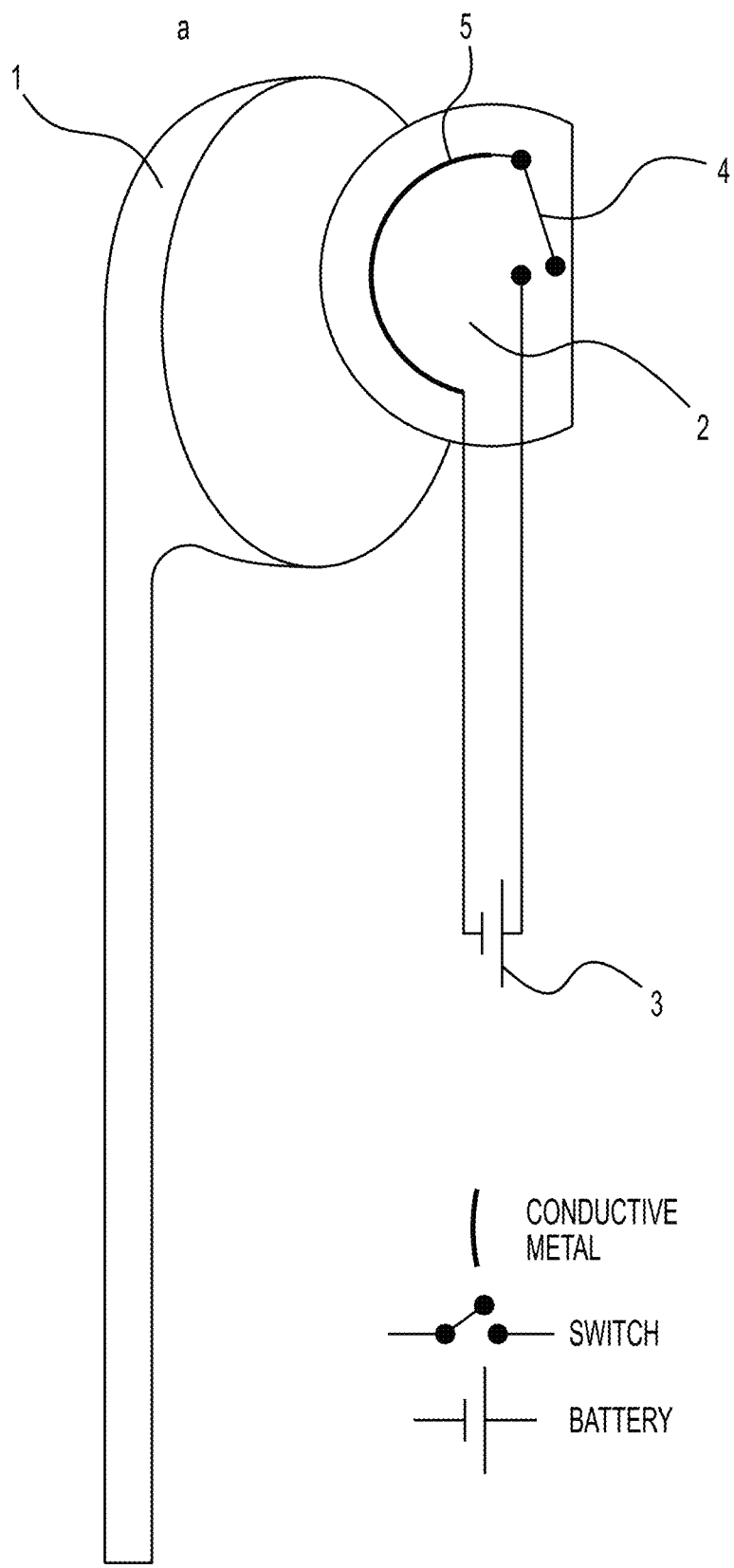
FIG. 2 is a drawing of an embodiment where the socket is made of a magnetic metal and the ball is made of a non-metal with a conductive metal placed inside it.
Figure 3:
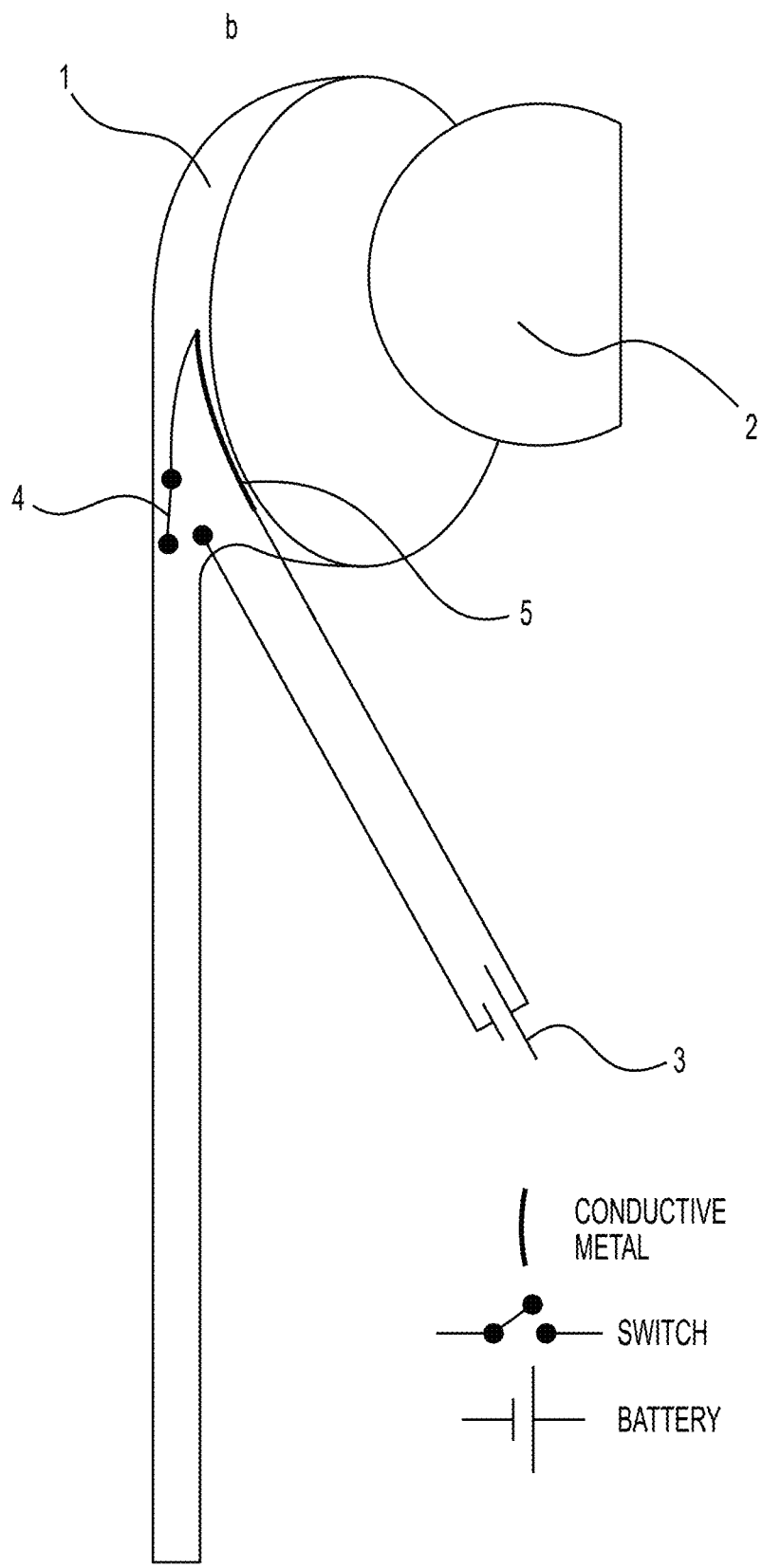
FIG. 3 is a drawing of an embodiment where the socket is made of a non-metal with a conductive metal placed inside it and the ball is made of a magnetic metal.

The embodiments of FIGS. 2 and 3 both fall within these configurations. According to the embodiment of FIG. 2, the socket (1) is made of a magnetic metal; otherwise, it would not be locked by the electromagnet. Further in this embodiment, the ball (2) can be made of a non-metal material, otherwise it could block the generated electromagnet inside it, including the conductive metal (5) and the microswitch (4). The battery (3) is located separately from the ball and the socket. This embodiment can be referred to as a metal/non-metal hybrid. According to this embodiment, the ball must be hollow to fit the conductive metal inside it. Further according to this embodiment, the electromagnetic field can be created by the internal conductive metal. In this embodiment, the conductive metal (5) can have any shape.

According to the embodiment of FIG. 3, the socket (1) can be made of a non-metal material, otherwise it could block the generated electromagnet inside it, including the conductive metal (5) and the microswitch (4). Further in this embodiment, the ball (2) is made of a magnetic metal; otherwise, it would not be locked by the electromagnet. The battery is located separately from the ball and the socket. This embodiment can be referred to as a metal/non-metal hybrid. According to this embodiment, the socket must be hollow to fit the conductive metal inside it. Further according to this embodiment, the electromagnetic field can be created by the internal conductive metal. In this embodiment, the conductive metal (5) can have any shape.

In certain embodiments, the present reversible electromagnetic locking element can have one or more of the following configurations:

the ball can comprise a metal which generates the electromagnetic field, with one wire connecting the metal of the ball to the microswitch and a second wire connecting the metal of the ball to the energy source, wherein the energy source is connected to the microswitch, with both the energy source and the microswitch being located separately from the ball; and the socket can comprise a metal which generates the electromagnetic field, with one wire connecting the metal of the socket to the microswitch and a second wire connecting the metal of the socket to the energy source, wherein the energy source is connected to the microswitch, with both the energy source and the microswitch being located separately from the socket.

Figure 4:
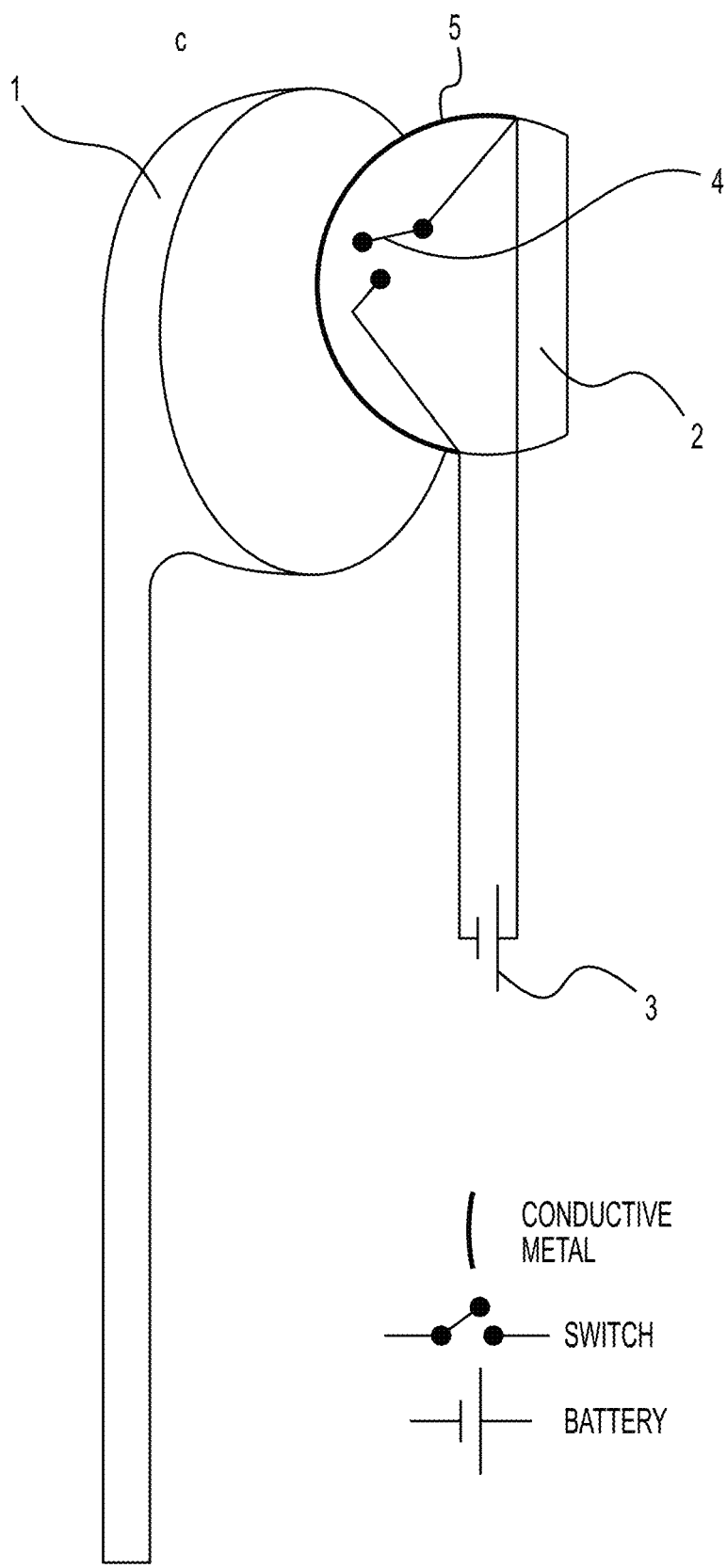
FIG. 4 is a drawing of an embodiment where the socket is made of a magnetic metal and the ball is made of a conductive metal with a thin coating layer of e.g., polyethylene on either of the ball or the socket. The ball in this configuration could be hollow or solid.
Figure 5:
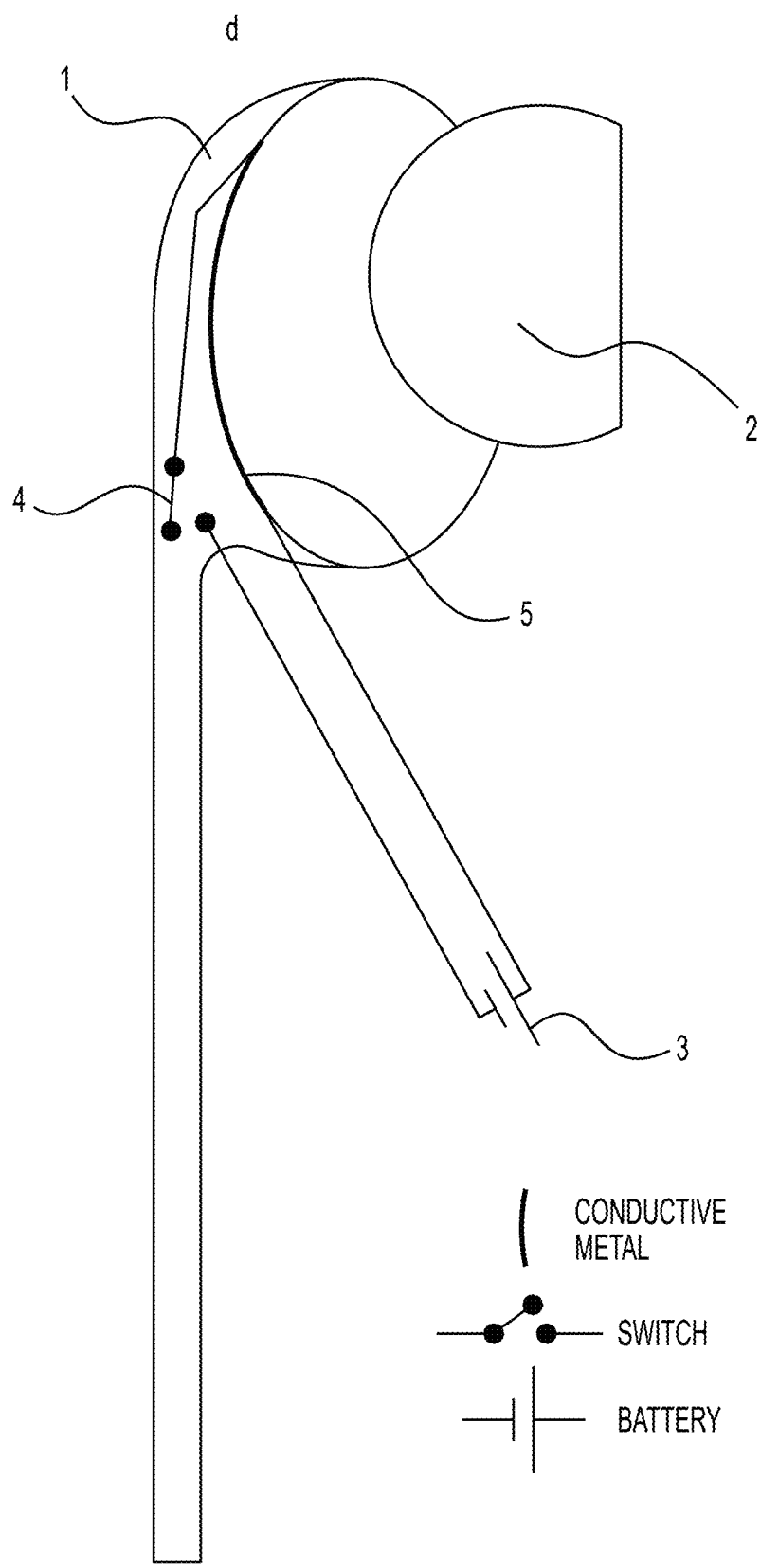
FIG. 5 is a drawing of an embodiment where the socket is made of a conductive metal and the ball is made of a magnetic metal with a thin coating layer of e.g., polyethylene on either of them. The socket in this configuration could be hollow or solid.

The embodiments of FIGS. 4 and 5 both fall within these configurations. According to the embodiment of FIG. 4, the socket (1) is made of a magnetic metal; otherwise, it would not be locked by the electromagnet. Further in this embodiment, the ball (2) can be made of a conductive metal to allow the generation of an electromagnet when connected to a battery. The conductive metal (5) must have a sufficient resistivity to avoid a short circuit at the ball (2). The battery (3) is located separately from the ball and the socket. In one embodiment, there may be a thin insulating material on the ball (2) or the conductive metal (5) to avoid any potential short circuit at the joint. According to this embodiment, the ball and the socket can both be hollow or solid. Further according to this embodiment, the electromagnetic field can be created by the conductive metal of the ball itself. In this embodiment, the conductive metal (5) is restricted to the shape of the ball (2).

According to the embodiment of FIG. 5, the socket (1) can be made of a conductive metal to allow the generation of an electromagnet when connected to a battery. The conductive metal (5) must have a sufficient resistivity to avoid a short circuit at the socket (1). Further in this embodiment, the ball (2) is made of a magnetic metal; otherwise, it would not be locked by the electromagnet. The battery (3) is located separately from the ball and the socket. In one embodiment, there may be a thin insulating material on the socket (1) or the conductive metal (5) to avoid any potential short circuit at the joint. According to this embodiment, the ball and the socket can both be hollow or solid. Further according to this embodiment, the electromagnetic field can be created by the conductive metal of the socket itself. In this embodiment, the conductive metal (5) is restricted to the shape of the socket (1).

It is to be noted that, according to one possible feature, in all the embodiments described above, the battery can be separate from the ball and the socket, such that it can be placed under the skin of the patient to enable easy recharging or replacement, as needed. In this regard, the battery can be connected to each of the electromagnet and the microswitch via wires such that the battery can be placed subcutaneously in the patient when the reversible electromagnetic locking element is placed inside the patient. In this regard, the battery can be configured for wireless charging or for easy replacement, similar to the procedure currently used with a pacemaker.

In another possible embodiment, the battery can be located with the ball or the socket.

It is to be further noted that the microswitch can be inside the ball, socket, or metal, or can be elsewhere, i.e., outside next to the battery, with the battery, or the like.

In certain embodiments, the ball can be configured to be attached to a shoulder blade of the patient and the socket can be configured to be attached to a head of a humerus of the patient. Likewise, in certain other embodiments, the ball can be configured to be attached to a head of a humerus of the patient and the plate can be configured to be attached to a shoulder blade of the patient.

In additional embodiments, the microswitch can be operated via a wireless remote control, Bluetooth, or through a wirelessly connected cellphone.

In further embodiments, the electromagnet can provide a frictionless locking mechanism.

In another embodiment, the present subject matter relates to a method for improving range of motion of a damaged shoulder joint in a patient, the method comprising: replacing a shoulder of the patient with a reversible electromagnetic locking element having a ball and socket configuration to assist operation of a glenohumeral joint (GHJ) in the patient, the reversible electromagnetic locking element comprising a ball, an electromagnet, a microswitch, and a metal with which the ball connects, wherein one of the ball and the socket is configured to be attached to a shoulder blade of the patient and the other of the ball and the socket is configured to be attached to a head of a humerus of the patient, wherein one of the ball and the socket is made of a magnetic metal or has the magnetic metal affixed thereto and the electromagnet is located with the other of the ball and the socket; providing an energy source comprising a battery to power the electromagnet; placing the glenohumeral joint at a desired angular position; selectively activating the electromagnet to exert an electromagnetic force between the ball and the socket such that the ball and the socket are locked via electromagnetism at a desired angular position about which an arm of the patient can freely move by switching the microswitch to an on position; and selectively deactivating the electromagnet to release the electromagnetic force between the ball and the socket, thereby unlocking the ball from the socket by switching the microswitch to an off position. In certain embodiments, either one of the ball and socket can be made of metal and the other one can be made of a non-metal, or both of the ball and socket can be made of metal, i.e., a metal ball and/or a metal socket. In certain embodiments, the present methods can be applied to patients having damage impacting the shoulder selected from the group consisting of nerve damage, advanced shoulder arthritis, a paralyzed or damaged deltoid, and any other damage that paralyzes arm or hand motion. According to these methods, the method can result in an increased range of motion of the patient's arm.

Another potential advantage of the present methods is that they can relieve pain in the patient and permit the patient to gain function in their arm that was previously lost due to the damage impacting the shoulder.

In use, the present methods can permit the arm of the patient to be locked at all possible angular positions, with the arm capable of moving freely about the desired angular position when locked in the desired angular position. In this regard, the electromagnet can be selectively deactivated, thereby unlocking the ball and the socket, to permit the arm to be placed at a different angular position prior to selectively activating the electromagnet, thereby locking the ball and the socket at the different angular position about which the arm can freely move, permitting the patient to conduct a different activity than was possible at the desired angular position. These methods can allow for significant improvement of shoulder motion of the patient, while not restricting passive motion of the shoulder when the electromagnet is deactivated.

Essentially, the patient can position their shoulder in whatever angle they wish to use and lock it in that position. By way of non-limiting example, if the patient wishes to bow hunt, the shoulder can be positioned in flexion internal rotation and locked in that position for the duration of the time they want to use their shoulder in this manner.

In this regard, the present methods can allow for significant improvement of shoulder motion of the patient in as little as six weeks after the shoulder of the patient is replaced with the reversible electromagnetic locking element. During these six weeks, the patent will have their shoulder immobilized to give the surrounding tissue time to heal before the new joint is used. This is in stark contrast to presently known solutions such as nerve reconstruction, which can have a recovery period of as long as one year before any effective results are seen. Even then, the patient may be barely able to move their shoulder according to the currently existing nerve reconstruction methods, even years after surgery, especially for patients having high level nerve injuries.

In a further embodiment of the present methods, the electromagnet can be deactivated at rest.

Unlike shoulder fusion, the present methods bypass the significant limitation of motion of the shoulder. The present dynamic reversible fusion devices and methods can allow articulation to mobilize the arm in a non-limited fashion, thereby allowing the passive movement of the arm in different directions and avoiding any significant pain around the scapulothoracic area and the neck.

The only limitation is the longevity of the battery in the implant, which can be bypassed by having a battery like that used for a heart pacemaker or other alternatives. In this regard, the battery can be located just under the skin so it can be easily recharged wirelessly, or even replaced with a small incision.

It is to be understood that the dynamic reversible electromagnetic locking element for locking the shoulder joint is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A reversible electromagnetic locking element having a ball and socket configuration assisting operation of a glenohumeral joint (GHJ) in a patient, comprising:
   a ball adapted for implantation on a surface of a glenoid of a patient;
   an electromagnet;
   a microswitch;
   an energy source comprising a battery to power the electromagnet; and
   a socket with which the ball connects, the socket being adapted for implantation in a humerus of the patient, wherein one of the ball and the socket is made of a magnetic metal or has the magnetic metal affixed thereto and the electromagnet is located with the other of the ball and the socket;
   wherein the microswitch is adapted to selectively activate the electromagnet to exert an electromagnetic force between the ball and the socket such that the ball and the socket, once implanted in the patient to assist the glenohumeral joint of the patient, are locked via magnetism at a desired angular position about which an arm of the patient can freely move when in an on position and, when the microswitch is in an off position, deactivate the electromagnet to release the electromagnetic force between the ball and the socket, thereby unlocking the ball from the socket at the desired angular position about which the arm of the patient can freely move when the microswitch is in the on position.

2. The reversible electromagnetic locking element of claim 1, wherein the electromagnet comprises a magnet and a conductive metal that can generate an electromagnetic field when connected to a battery.

3. The reversible electromagnetic locking element of claim 2, having a configuration selected from the group consisting of:
   the conductive metal and the microswitch are both located with the ball and the socket is made of the magnetic metal or has the magnetic metal affixed thereto;

the conductive metal and the microswitch are both located with the socket and the ball is made of the magnetic metal or has the magnetic metal affixed thereto;

the conductive metal is located with the ball, with one wire connecting the conductive metal to the microswitch and a second wire connecting the conductive metal to the energy source, wherein the energy source is connected to the microswitch, with both the energy source and the microswitch being located separately from the ball, and the socket is made of the magnetic metal or has the magnetic metal affixed thereto; and the conductive metal is located with the socket, with one wire connecting the conductive metal to the microswitch and a second wire connecting the conductive metal to the energy source, wherein the energy source is connected to the microswitch, with both the energy source and the microswitch being located separately from the socket, and the ball is made of the magnetic metal or has the magnetic metal affixed thereto.

4. The reversible electromagnetic locking element of claim 2, wherein the ball or the socket contains the conductive metal used as the electromagnet to generate the electromagnetic field.

5. The reversible electromagnetic locking element of claim 4, having a configuration selected from the group consisting of:

the ball comprises the conductive metal which generates the electromagnetic field, with one wire connecting the ball to the microswitch and a second wire connecting the ball to the energy source, wherein the energy source is connected to the microswitch, with both the energy source and the microswitch being located separately from the ball; and the socket comprises the conductive metal which generates the electromagnetic field, with one wire connecting the socket to the microswitch and a second wire connecting the socket to the energy source, wherein the energy source is connected to the microswitch, with both the energy source and the microswitch being located separately from the socket.

6. The reversible electromagnetic locking element of claim 1, wherein the battery is located with the ball or the socket.

7. The reversible electromagnetic locking element of claim 1, wherein the battery is located separately from the ball and the socket and is connected to each of the electromagnet and the microswitch via wires such that the battery can be placed subcutaneously in the patient and configured for wireless charging, when the reversible electromagnetic locking element is placed inside the patient, wherein the battery can be replaced with a small incision.

8. The reversible electromagnetic locking element of claim 1, wherein the battery is a replaceable battery located separately from the ball and the socket and is connected to each of the electromagnet and the microswitch via wires such that the battery can be placed subcutaneously in the patient when the reversible electromagnetic locking element is placed inside the patient, wherein the battery can be replaced with a small incision.

9. The reversible electromagnetic locking element of claim 1, wherein the ball is configured to be attached to a shoulder blade of the patient and the socket is configured to be attached to a head of a humerus of the patient.

10. The reversible electromagnetic locking element of claim 1, wherein the microswitch is operated via a wireless remote control, Bluetooth, or through a wirelessly connected cellphone.

11. The reversible electromagnetic locking element of claim 1, wherein the electromagnet provides a frictionless locking mechanism.

12. A method for improving range of motion of a damaged shoulder joint in a patient, the method comprising:

replacing a shoulder of the patient with a reversible electromagnetic locking element having a ball and socket configuration to assist operation of a glenohumeral joint (GHJ) in the patient, the reversible electromagnetic locking element comprising a ball, an electromagnet, a microswitch, and a socket with which the ball connects, wherein one of the ball and the socket is made of a magnetic metal or has the magnetic metal affixed thereto and the electromagnet is located with the other of the ball and the socket, wherein the ball is adapted to be implanted on a surface of a glenoid of the patient, and wherein the socket is adapted to be implanted in a humerus of the patient;

providing an energy source comprising a battery to power the electromagnet;

placing the glenohumeral joint at a desired angular position;

selectively activating the electromagnet to exert an electromagnetic force between the ball and the socket such that the ball and the socket are locked via electromagnetism at a desired angular position about which an arm of the patient can freely move by switching the microswitch to an on position; and configured to selectively adjust the arm of the patient to lock in one of a desired plurality of angular positions selectively deactivating the electromagnet to release the electromagnetic force between the ball and the socket, thereby unlocking the ball from the socket by switching the microswitch to an off position.

13. The method of claim 12, wherein the patient has damage impacting the shoulder that is a paralyzed or damaged deltoid or any other damage that paralyzes arm or hand motion, and wherein the method results in an increased range of motion of the patient's arm.

14. The method of claim 13, wherein the method relieves pain in the patient and permits the patient to gain function in their arm that was previously lost due to the damage impacting the shoulder.

15. The method of claim 12, wherein the method permits the arm of the patient to be locked at all possible angular positions, with the arm capable of moving freely about the desired angular position when locked in the desired angular position.

16. The method of claim 12, wherein the electromagnet is selectively deactivated, thereby unlocking the ball and the socket, to permit the arm to be placed at a different angular position prior to selectively activating the electromagnet, thereby locking the ball and the socket at the different angular position about which the arm can freely move, permitting the patient to conduct a different activity than was possible at the desired angular position.

17. The method of claim 12, wherein the method allows for significant improvement of shoulder motion of the patient, while not restricting passive motion of the shoulder when the electromagnet is deactivated.

18. The method of claim 17, wherein the method allows for significant improvement of shoulder motion of the patient six weeks after the shoulder of the patient is replaced with the reversible electromagnetic locking element.

19. The method of claim 17, wherein the electromagnet is deactivated at rest.

\* \* \* \* \*

UNITED STATES PATENT AND TRADEMARK OFFICE
CERTIFICATE OF CORRECTION

| | |
|---|---|
| PATENT NO. | : 11,974,929 B1 |
| APPLICATION NO. | : 18/200172 |
| DATED | : May 7, 2024 |
| INVENTOR(S) | : Alya A. Arabi, Bassem T. Elhassan and Ali O. Arabi |

It is certified that error appears in the above-identified patent and that said Letters Patent is hereby corrected as shown below:

On the Title Page

Item (72) Inventors, please add the third Inventor "ALI O. ARABI, Al Ain (AE)".

Signed and Sealed this
Eighteenth Day of June, 2024

Katherine Kelly Vidal
*Director of the United States Patent and Trademark Office*